April 9, 1968 H. C. SWIM Plant Pat. 2,802
CAMELLIA PLANT
Filed Jan. 6, 1967
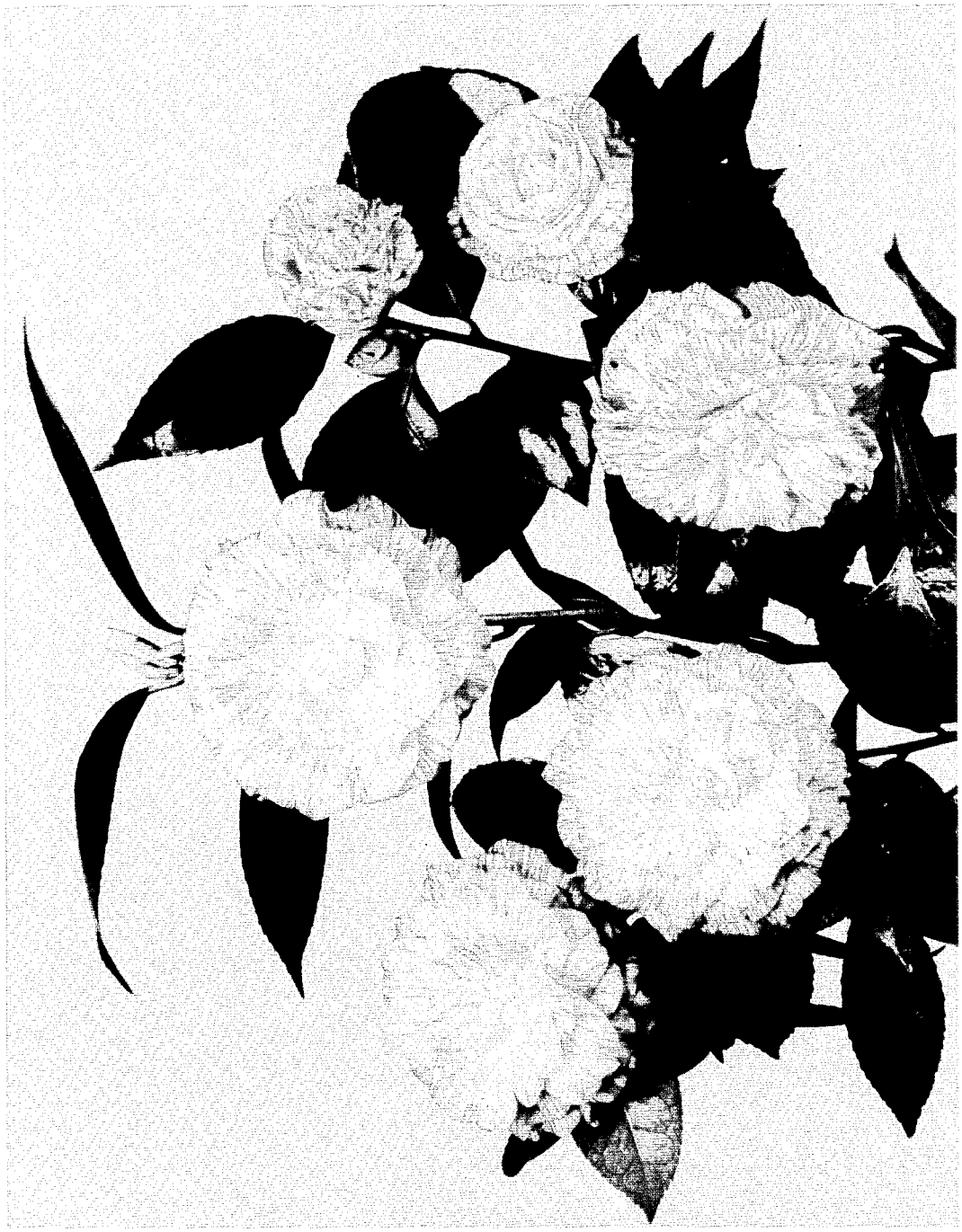
Inventor.
H. C. Swim
By: Robb & Robb
Attorneys.

United States Patent Office

Plant Pat. 2,802
Patented Apr. 9, 1968

2,802
CAMELLIA PLANT

Herbert C. Swim, Ontario, Calif., assignor to Armstrong Nurseries, Inc., Ontario, Calif., a corporation of California Filed Jan. 6, 1967, Ser. No. 607,867
1 Claim. (Cl. Plt.—60)

The present invention relates to a new and distinct variety of camellia plant of the *Camellia japonica* class, which was originated by me by crossing the *Camellia japonica* variety known as "Lady Vansittart" (unpatented) with the *Camellia japonica* variety known as "Daikagura" (unpatented), the former being the seed parent and the latter being the pollen parent.

The general objective of this breeding was to produce a new and improved camellia variety having an extended blooming season ranging from early to late, combined with a vigorous and attractive plant habit and a distinctive and interesting flower color and form. This objective was fully achieved, along with other desirable features, as evidenced by the following unique combination of features which are outstanding in the new variety and which distinguish it from its parents, as well as from all other varieties of which I am aware:

(1) A vigorous, upright-spreading and rather bushy plant habit, with attractive, large and dark green foliage;

(2) A moderate to abundant floriferousness, with the flowers borne singly and usually terminally, but sometimes axially, near the end of the shoots;

(3) An attractive, formal-double flower form varying from near perfectly imbricated to a somewhat irregular petal arrangement, with a small cone of petals remaining unopened and no stamens present, but with some flowers being very double rose form and having a few stamens showing at the center;

(4) A distinctive, interesting and attractive color between white and very light pink, marked lengthwise on the petals with many small to medium sized irregular streaks, often interspersed with many small specks, all of closely similar but varying shades of Carmine and Crimson; and (5) A long blooming period ranging from February to late April in southern California.

The seed parent "Lady Vansittart" has an upright and vigorous plant habit, with attractive, glossy, lanceolate, dark green, holly-like foliage, and bears semi-double flowers from about 10 cm. to 11 cm. wide by about half as high when fully expanded, while the flower form is quite regular, generally symmetrical and imbricated, with the central stamens showing very readily. Its flowers are dark pink in color and the blooming period ranges from mid-season to late. In comparison with this parent, the new variety has a more semi-spreading plant habit, instead of the more upright habit of the parent; the flowers of the new variety are formal-double, whereas those of this parent are rose form; and the flower color is white, streaked and flecked with pink and light red, whereas the flowers of the parent are dark pink.

The pollen parent "Daikagura" has a moderately vigorous, semi-spreading plant habit, with large, attractive, glossy, dark green foliage, and bears large flowers of from 10 cm. to 12 cm. in diameter, and which are pink, splotched with white in color. The flowers are double, and have a quite irregular peony form, while the blooming period is early. As compared with this parent, the new variety has a blooming period from February to late April in southern California, whereas this parent variety blooms from late October through early January; the flower form of the new variety is formal-double, instead of having an irregular, peony form like the parent; and the flower color of the new variety is white, streaked and flecked with varying shades of pink and light red, whereas the flowers of "Daikagura" variety are pink, splotched with white.

A sexual reproduction of my new variety by both grafting and by cuttings, as performed at Ontario, Calif., shows that the foregoing characteristics and distinctions come true and are established and transmitted through succeeding propagations.

The accompanying drawings shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)) and Robert Ridgway's Color Standards and Nomenclature (hereinafter abbreviated as (R)), as indicated:

Type: Ornamental; flowering evergreen shrub; for general landscape use and for cut flowers.
Class: *Camellia japonica* type.
Breeding: Seedling.
*Seed parent.*—"Lady Vansittart."
*Pollen parent.*—"Daikagura."
Propagation: Holds its distinguishing characteristics through succeeding propagations by both grafting and cuttings.

*Plant*

Growth:
*Habit.*—Upright-spreading; from moderately to much-branched.
*Vigor.*—Vigorous.
*New stems.*—Medium caliper; glabrous. Color—between Apple Green, Plate XVII (R) and Chromium Green, Plate XXXII (R).
*Older stems.*—Glabrous; bark becoming fissured and scurfy. Color—between Mikado Brown, Plate XXIX (R) and Fawn Color, Plate XL (R).
*Mature branches.*—Rough and scurfy when a year or two old, becoming more smooth as original bark is sloughed off. Color—between Wood Brown, Plate XL (R) and Light Drab, Plate XLVI (R). Light Drab, Plate XLVI (R).

Leaves:
*Habit.*—Abundant.
*Texture.*—Thick; leathery.
*Size.*—Between medium and large; from 4½ cm. to 5½ cm. wide and from 9 to 11 cm. long.
*Petiole.*—From average to large caliper; from 8 to 12 mm. in length; sometimes with a shallow groove along upper surface; glabrous.
*Shape.*—Varying between oval, obovate and ovate. Apex—usually extended and acute. Margin—usually simply serrate and entire near petiole attachment.
*Upper surface.*—Glossy. Color: mature—between Empire Green, Plate XXXII (R) and Dark American Green, Plate XLI (R), with main veins near Courge Green, Plate XVII (R).
*Lower surface.*—Glossy. Color: mature—between Light Bice Green, Plate XVII (R) and Chromium Green, Plate XXXII (R), with veins near Empire Green, Plate XXXII (R).

*Flower*

Flower borne: Sessile; mostly terminal, with a few axillary near end of shoot; usually single, but sometimes double when terminal.
Quantity of bloom: Between moderate and abundant.
Time of bloom: One long season, usually from February to April at Ontario, Calif.

Fragrance: From none to slight.

Bud:

*Size.*—Small to medium size.

*Form.*—Usually between globular and ovoid.

*Sepals.*—Numerous; usually from 10 to 14; increas- in size from the outermost which are nearly round, to the innermost which are between round and broadly obovate and usually slightly pointed at apex; the two innermost sepals showing transition to petals with streaks of white and red petal tissue. Surface—pubescent; color—between Courge Green, Plate XVII (R) and Biscay Green, Plate XVII (R).

*Opening.*—Opens up well.

Bloom:

*Size (when fully open).*—Medium; from 8 cm. to 10 cm. in diameter.

*Petalage.*—Very double; usually from 50 to 70 petals, with central petals or petaloids progressively smaller to center.

*Form.*—Flowers just opening are usually cupped, with outer and intermediate petals often slightly reflexed outward near apex, but sometimes inward; mature flower form is usually a complete formal double, varying from near perfectly imbricated to somewhat irregular petal arrangement, with a small central cone of small petals or petaloids remaining unopened and no stamens present; some flowers are very double rose form with a few stamens showing at the center, often mixed with petaloids; outer petals of all flowers are strongly reflexed outward; inner petals are more cupped, and sometimes margins showing a tight inward curl under some conditions.

*Petals.*—Thickness — moderate. Surfaces — satiny, both inside and outside. Shape—somewhat irregular; petaloids usually irregular and mostly narrowly obovate; outer petals—between round and broadly obovate; intermediate petals—between round and obovate; inner petals—usually obovate.

*Color.*—Newly opened flower; outer petals—outside surface—between white and Venetian Pink, Plate 420/3, page 125 (W), marked lengthwise on the petal with many small to medium sized irregular streaks, interspersed with many small specks, all of closely similar but apparently varying color from near Carmine, Plate 21/3, page 21 (W) to near Crimson, Plate 22/1, page 22 (W); inside surface—same as outside surface; inner petals—same as outer petals. 2–3 days open flower: outer petals—outside surface—between white and Rose Pink, Plate 427/3, page 126 (W), with the streaks and specks varying from near Crimson, Plate 22/3 page 22 (W) to near Rose Madder, Plate 23/1, page 23 (W); inside surface—same as outside surface; inner petals—same as outer petals.

*General color effect.*—Newly opened flower—near white, with small streaks and specks radiating from center of between Carmine, Plate 21/3, page 21 (W) and Crimson, Plate 22/3, page 22 (W). 2–3 days open flower—near white, with streaks and specks of between Crimson, Plate 22/3, page 22 (W) and Rose Madder, Plate 23/3, page 23 (W).

*Behavior.*—Flowers persist on plant as they become old.

*Longevity.*—On plant in garden—from 4 to 8 days during March. Cut flowers grown outdoors and kept at living room temperature—from 3 to 6 days.

*Reproductive organs*

Stamens: In flowers with stamens, usually from 15 to 30 in number; most with anthers. Length—from 5 mm. to 18 mm.

Filaments: Color—near Naples Yellow, Plate 403/3, page 121 (W).

Anthers: Color—near Lemon Yellow, Plate 4/2, page 4 (W).

Pistils: Usually 5; from 5 mm. to 15 mm. long. Color—near Sap Green, Plate 62/2, page 62 (W).

Seed pods: None observed.

I claim:

1. A new and distinct variety of camellia plant of the *Camellia japonica* class, substantially as herein shown and described, characterized particularly as to novelty by the unique combination of a vigorous, upright-spreading and rather bushy plant habit, with attractive, large and dark green foliage, a moderate to abundant floriferousness, with the flowers borne singly and usually terminally, but sometimes axillary, near the end of the shoots, an attractive, formal-double flower form varying from near perfectly imbricated to a somewhat irregular petal arrangement, with a small cone of petals remaining unopened and no stamens present, but with some flowers being very double rose form and having a few stamens showing at the center, a distinctive, interesting and attractive color between white and very light pink, marked lengthwise on the petals with many small to medium sized irregular streaks, often interspersed with many small specks, all of closely similar but varying shades of Carmine and Crimson, and a long blooming period ranging from February to late April in southern California.

No references cited.

ROBERT E. BAGWELL, *Primary Examiner.*